United States Patent
Taniguchi et al.

(10) Patent No.: US 6,391,915 B2
(45) Date of Patent: *May 21, 2002

(54) PROPANOLAMINE DERIVATIVES

(75) Inventors: Kiyoshi Taniguchi, Kobe; Minoru Sakurai, Toyonaka; Norio Hashimoto, Ibaraki; Takumi Okamoto, Toyonaka; Kazunori Tsubaki, Uji; Yasuyo Tomishima, Osaka; Hisashi Takasugi, Sakai, all of (JP)

(73) Assignee: Fujisawa Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/380,608
(22) PCT Filed: Mar. 17, 1998
(86) PCT No.: PCT/JP98/01112
§ 371 Date: Sep. 15, 1999
§ 102(e) Date: Sep. 15, 1999
(87) PCT Pub. No.: WO98/41497
PCT Pub. Date: Sep. 24, 1998

(30) Foreign Application Priority Data

Mar. 17, 1997 (AT) .............................................. PO5659

(51) Int. Cl.$^7$ ......................... A01N 37/12; A01N 37/44; A61K 31/195; C07C 229/40; C07C 229/42

(52) U.S. Cl. .......................... 514/510; 514/567; 560/43; 560/45; 562/452
(58) Field of Search ................................. 514/510, 567; 560/43, 45; 562/452

(56) References Cited

U.S. PATENT DOCUMENTS 5,254,595 A * 10/1993 Guzzi et al. ................. 514/652
5,387,710 A    2/1995 Shiokawa et al.

* cited by examiner

Primary Examiner—Brian J. Davis
(74) Attorney, Agent, or Firm—Oblon, Spivak, McClelland, Maier & Neustadt, P.C.

(57) ABSTRACT

This invention relates to new propanolamine derivatives presented by the following formula [I]:

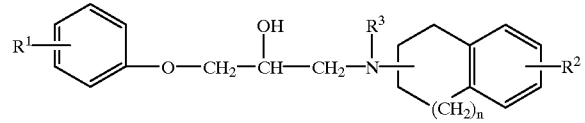

wherein $R^1$ hydrogen or lower alkenyloxy, $R^2$ is carboxy (lower)alkoxy or protected carboxy(lower)alkoxy, $R^3$ is hydrogen or N-protective group, n is an integer of 1 or 2, and salts thereof which have gut selective sympathomimetic, anti-ulcerous, anti-pancreatitis, lipolytic and anti-pollakisuria activities, to processes for the preparation thereof and to a pharmaceutical composition comprising the same.

5 Claims, No Drawings

PROPANOLAMINE DERIVATIVES

This application is a 371 of PCT/JP98/01112 filed Mar. 17, 1998.

1. Technical Field

This invention relates to new propanolamine derivatives and salts thereof which are useful as a medicament.

2. Background Art

Some propanolamine derivatives having spasmolytic activity and relaxing activity on smooth muscle contraction have known as described, for example, in PCT International Publication WO94/25427.

DISCLOSURE OF INVENTION

This invention relates to new propanolamine derivatives and salts thereof.

More particularly, it relates to new propanolamine derivatives and salts thereof which have gut selective sympathomimetic, anti-ulcerous, anti-pancreatitis, lipolytic and anti-pollakisuria activities, to processes for the preparation thereof, to a pharmaceutical composition comprising the same and to a method of using the same therapeutically in the treatment and/or prevention of gastro-intestinal disorders caused by smooth muscle contractions in human beings or animals, and more particularly to a method for the treatment and/or prevention of spasm or hyperanakinesia in case of irritable bowel syndrome, gastritis, gastric ulcer, duodenal ulcer, enteritis, cholecystopathy, cholangitis, urinary calculus and the like; for the treatment and/or prevention of ulcer such as gastric ulcer, duodenal ulcer, peptic ulcer, ulcer caused by non steroidal anti-inflammatory drugs, or the like; for the treatment and/or prevention of dysuria such as pollakisuria, urinary incontinence or the like in case of nervous pollakisuria, neurogenic bladder dysfunction, nocturia, unstable bladder, cystospasm, chronic cystitis, chronic prostatitis or the like; and for the treatment and/or prevention of pancreatitis, obesity, diabetes, glycosuria, hyperlipidemia, hypertension, atherosclerosis, glaucoma, melancholia, depression and the like.

One object of this invention is to provide new and useful propanolamine derivatives and salts thereof which have gut selective sympathomimetic, anti-ulcerous, lipolytic and anti-pollakisuria activities.

Another object of this invention is to provide processes for the preparation of said propanolamine derivatives and salts thereof.

A further object of this invention is to provide a pharmaceutical composition comprising, as an active ingredient, said propanolamine derivatives and salts thereof.

Still further object of this invention is to provide a therapeutical method for the treatment and/or prevention of aforesaid diseases in human beings or animals, using said propanolamine derivatives and salts thereof.

The object propanolamine derivatives of this invention are new and can be represented by the following general formula [I]:

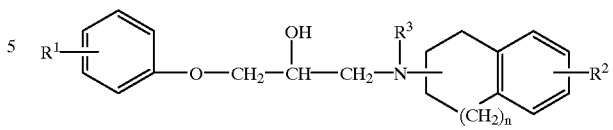

wherein $R^1$ is hydrogen or lower alkenyloxy, $R^2$ is carboxy(lower)alkoxy or protected carboxy(lower)alkoxy, $R^3$ is hydrogen or N-protective group, n is an integer of 1 or 2, and salts thereof (Hereinafter, these propanolamine derivatives may be mentioned as the object compound [I]).

The object compound [I] or its salt can be prepared by the following processes.

Process 1

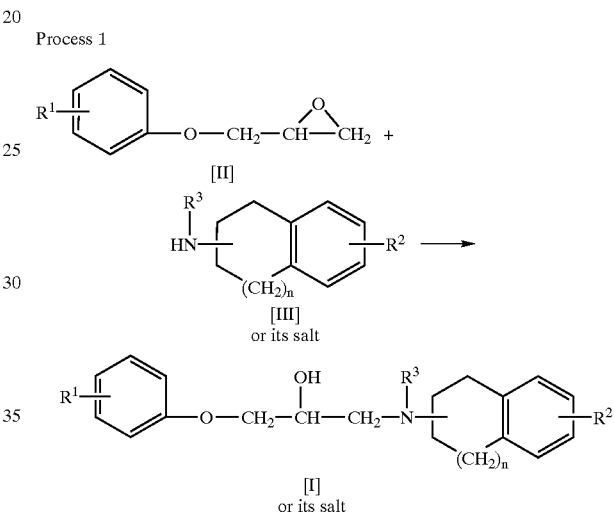

Process 2

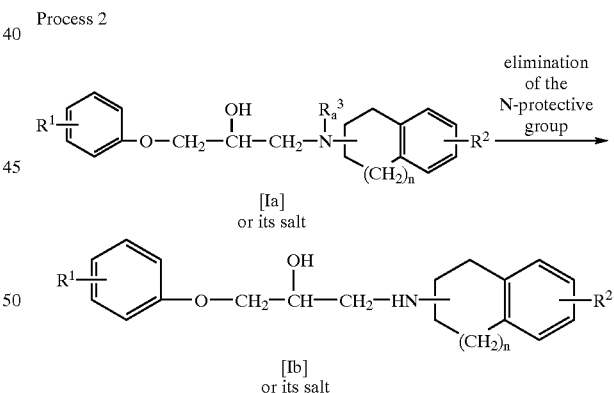

wherein $R^1$, $R^2$, $R^3$ and n are each as defined above, and $R_a^3$ is N-protective group.

In the above and subsequent description of the present specification, suitable examples of the various definition to be included within the scope of the invention are explained in detail in the following.

The term "lower" is intended to mean a group having 1 to 6 carbon atom(s), unless otherwise provided.

Suitable "lower alkenyl" moiety in the term "lower alkenyloxy" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, methylvinyl, ethylvinyl, 1-(or 2- or 3-)- methyl-1-(or 2-)propenyl, 1-(or 2- or 3-)ethyl-1-(or 2-)-propenyl, 1-(or 2- or 3- or 4-)methyl-1-(or 2- or 3-)butenyl, and the like, in which preferable example may be $C_2$–$C_4$ alkenyl, and more preferable example may be propenyl.

Suitable "lower alkoxy" moiety in the terms of "carboxy (lower)alkoxy" and "protected carboxy(lower)alkoxy" may be a straight or branched one such as methoxy, ethoxy, propoxy, isopropoxy, butoxy, pentyloxy or the like, in which preferable one is $C_1$–$C_4$ ones and more preferably methoxy.

Suitable "protected carboxy" moiety in the term "protected carboxy(lower)alkoxy" may include esterified carboxy and the like. And suitable example of said esterified carboxy may be substituted or unsubstituted lower alkoxycarbonyl [e.g. methoxycarbonyl, ethoxycarbonyl, propoxycarbonyl, butoxycarbonyl, hexyloxycarbonyl, 2-iodoethoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, etc.] and the like, in which preferable one is lower alkoxycarbonyl.

"N-Protective group" may be common N-protective group such as acyl, for example, substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxycarbonyl, etc.], substituted or unsubstituted aralkyloxycarbonyl [e.g. benzyyloxycarbonyl, p-nitrobenzyloxycarbonyl, etc.], substituted or unsubstituted arenesulfonyl [e.g. benzenesulfonyl, tosyl, etc.], nitrophenylsulfenyl, ar(lower)alkyl [e.g. trityl, benzyl, etc.] or the like, in which preferable one is phenyl(lower)alkyl such as benzyl.

Preferred embodiments of the object compound [I] are as follows:

$R^1$ is hydrogen or lower alkenyloxy, $R^2$ is carboxy(lower)alkoxy or esterified carboxy(lower)alkoxy, $R^3$ is hydrogen or ar(lower)alkyl, and n is an integer of 1 or 2.

More preferred embodiments of the object compound [I] are as follows:

$R^1$ is hydrogen or lower alkenyloxy, $R^2$ is lower alkoxycarbonyl(lower)alkoxy, $R^3$ is hydrogen or benzyl, and n is an integer of 1 or 2 (more preferably an integer of 2).

Suitable salts of the object propanolamine derivatives [I] are pharmaceutically acceptable salts and include conventional non-toxic salts such as an inorganic acid addition salt [e.g. hydrochloride, hydrobromide, sulfate, phosphate, etc.], an organic acid addition salt [e.g. formate, acetate, trifluoroacetate, oxalate, maleate, fumarate, tartrate, methanesulfonate, benzenesulfonate, toluenesulfonate, etc.], an alkali metal salt [e.g. sodium salt, potassium salt, etc.] or the like.

The processes for preparing the object compound [I] are explained in detail in the following.

Process 1

The object compound [I] or its salt can be prepared by reacting a compound [II] with a compound [III] or its salt.

Suitable salt of the compound [III] may be the same as those exemplified for the compound [I].

The reaction is preferably carried out in the presence of a base such as an alkali metal carbonate [e.g. sodium carbonate, potassium carbonate, etc.], an alkaline earth metal carbonate [e.g. magnesium carbonate, calcium carbonate, etc.], an alkali metal bicarbonate [e.g. sodium bicarbonate, potassium bicarbonate, etc.], tri(lower) alkylamine [e.g. trimethylamine, triethylamine, etc.], picoline or the like.

The reaction is usually carried out in a conventional solvent, such as an alcohol [e.g. methanol, ethanol, propanol, isopropanol, etc.], diethyl ether, tetrahydrofuran, dioxane, or any other organic solvent which does not adversely influence the reaction.

The reaction temperature is not critical, and the reaction can be carried out under cooling to heating.

Process 2

The object compound [Ib] or its salt can be prepared by subjecting a compound [Ia] or its salt to elimination reaction of the N-protective group.

Suitable salts of the compounds [Ia] and [Ib] may be the same as those exemplified for the compound [I].

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.] and an acid addition salt compound [e.g. pyridine hydrochloride, etc.].

The elimination using trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

In case that the N-protective group is benzyl, the reduction is preferably carried out in the presence of a combination of palladium catalysts [e.g. palladium black, palladium on carbon, etc.] and formic acid or its salt [e.g. ammonium formate, etc.].

The reduction is usually carried out in a conventional solvent which does not adversely influence the reaction such as water, an alcohol [e.g. methanol, ethanol, propanol, etc.], chlqrobenzene, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc. or a mixture thereof.

The reaction temperature of this reduction is not critical and the reaction is usually carried out under cooling to heating.

The compounds obtained by the above processes can be isolated and purified by a conventional method such as pulverization, recrystallization, column chromatography, reprecipitation, or the like, and converted to the desired salt in conventional manners, if necessary.

It is to be noted that the compound [I] and the other compounds may include one or more stereoisomers due to asymmetric carbon atoms, and all of such isomers and mixture thereof are included within the scope of this invention.

It is further to be noted that isomerization or rearrangement of the object compound [I] may occur due to the effect of the light, acid, base or the like, and the compound obtained as the result of said isomerization or rearrangement is also included within the scope of the present invention.

It is also to be noted that the solvating form of the compound [I] (e.g. hydrate, etc.) and any form of the crystal of the compound [I] are included within the scope of the present invention.

The object compound [I] and salts thereof possess gut selective sympathomimetic, anti-ulcerous, anti-pancreatitis, lipolytic and anti-pollakisuria activities, and are useful for the treatment and/or prevention of gastrointestinal disorders caused by smooth muscle contractions in human beings or animals, and more particularly to methods for the treatment and/or prevention of spasm or hyperanakinesia in case of irritable bowel syndrome, gastritis, gastric ulcer, duodenal ulcer, enteritis, cholecystopathy, cholangitis, urinary calculus and the like; for the treatment and/or prevention of ulcer such as gastric ulcer, duodenal ulcer, peptic ulcer, ulcer caused by non steroidal anti-inflammatory drugs, or the like; for the treatment and/or prevention of dysuria such as pollakisuria, urinary incontinence or the like in case of nervous pollakisuria, neurogenic bladder dysfunction, nocturia, unstable bladder, cystospasm, chronic cystitis, chronic prostatitis or the like; and for the treatment and/or prevention of pancreatitis, obesity, diabetes, glycosuria, hyperlipidemia, hypertension, atherosclerosis, glaucoma, melancholia, depression and the like.

In order to illustrate the usefulness of the object compound [I], the pharmacological data of the object compound [I] are shown in the following.

Test 1

Effect on isolated rat distal colon:

(1) Test Method

Male SD rats (180–230 g) were used. Animals were fasted for 24 hours prior to experiment. Distal colon was removed immediately after sacrifice and placed in an organ bath containing 25 ml Tyrode solution aerating with 95% $O_2$, 5% $CO_2$ at 37° C. The strip was mounted under 0.5 g tension and spontaneous contractions were recorded isometrically. After the mobility was of a uniform size, test compound was added to an organ bath and the contractions were observed over a 30 minutes period. Effect of test compound was calculated by comparing contractions before and after test compound.

(2) Test Result

| Test Compound (Example No.) | $IC_{50}$ (M) |
|---|---|
| 1 | $4.2 \times 10^{-9}$ |

Test 2

Effect on isolated non-pregnant rat uterus (1) Test Method

Female SD rats (150–180 g) were used. 48 and 24 hours prior to use, rats were given estradiol (ovahormon benzoat Trademark, Teikoku Hormone Mfg. Co., Ltd.) subcutaneously at a dose of 40 $\mu$g/rat to induce oestrus. The animals were killed and uteri were removed. Each strip was placed in an organ bath containing 25 ml Locke solution aerating with 95% $O_2$, 5% $CO_2$ at 37° C. under 1 g tension. Contractions were recorded isometrically. After the spontaneous contractions were of a uniform size, test compound was added to organ bath. The motility was observed over a 20 minutes period. Effect of test compound was calculated by comparing contractions before and after test compound.

(2) Test Result

| Test Compound (Example No.) | $IC_{50}$ (M) |
|---|---|
| 1 | $3.7 \times 10^{-7}$ |

For therapeutic purpose, the compound [I] and a salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral or external (topical) administration. The pharmaceutical preparations may be capsules, tablets, dragees, granules, suppositories, solutions, lotion, inhalant, ophthalmic preparations, suspension, emulsion, ointment, gel, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

The following Preparations and Examples are given for the purpose of illustrating this invention.

Preparation 1

A suspension of (2S)-3-phenoxy-1,2-epoxypropane (300 mg) (IL FARMACO, 50 (10), 643 (1995)), N-benzyl-(1-hydroxy-6,7,8,9-tetrahydro-5H-benzocyclohepten-6-yl)amine (535 mg), and ytterbium(III) trifluoromethanesulfonate (372 mg) in dichloromethane (15 ml) was stirred at room temperature for 3 days and partitioned between ethyl acetate and aqueous sodium bicarbonate. The organic layer was separated, washed with brine, dried over sodium sulfate, and evaporated in vacuo. The residue was chromatographed (dichloromethane-methanol) over silica gel (16 g) to afford (2S)-1-[N-benzyl-(6,7,8,9-tetrahydro-1-hydroxy-5H-benzocyclohepten-6-yl)amino]-3-phenoxy-2-propanol (747 mg) as a colorless oil.

IR (KBr): 3359, 1244 cm$^{-1}$; NMR (CDCl$_3$, δ): 1.15–1.35 (1H, m), 1.55–2.4 (5H, m), 2.55–3.35 (6H, m), 3.64–3.98 (4H, m), 4.85 (1H, br), 6.58 (1H, d, J=8.0 Hz), 6.75 (1H, d, J=7.4 Hz), 6.82–6.99 (4H, m), 7.15–7.31 (8H, m); (+) APCI MS m/z: 418 (M$^+$+1).

Preparation 2

The following compound was obtained according to a similar manner to that of Preparation 1.

(2S)-1-[N-Benzyl-(6,7,8,9-tetrahydro-2-hydroxy-5H-benzocyclohepten-6-yl)amino]-3-phenoxy-2-propanol IR (KBr): 3386, 1244 cm$^{-1}$; NMR (CDCl$_3$, δ): 1.2–2.3 (5H, m), 2.45–3.07 (6H, m), 3.64–4.11 (5H, m), 4.0 (1H, br), 6.51–6.60 (2H, m), 6.82–7.01 (4H, m), 7.21–7.30 (8H, m); (+) APCI MS m/z: 418 (M$^+$+1).

EXAMPLE 1

A suspension of 60% sodium hydride (54 mg, washed with n-hexane) in N,N-dimethylformamide (1 ml) was added slowly to a stirred solution of (2S)-1-[N-benzyl-(6,7,8,9-tetrahydro-1-hydroxy-5H-benzocyclohepten-6-yl)amino]-3-phenoxy-2-propanol (512 mg) in N,N-dimethylformamide (5 ml) under ice cooling and the resulting mixture was stirred at the same temperature for 30 minutes. A solution of ethyl bromoacetate (225 mg) in N,N-dimethylformamide (1 ml) was added dropwise therein at the same temperature and the mixture was stirred at the same temperature for 4 hours. The reaction mixture was diluted with water and extracted with ethyl acetate. The extract was washed twice with brine, dried over magnesium sulfate, and evaporated in vacuo to afford (2S)-1-[N-benzyl-(1-ethoxycarbonylmethoxy-6,7,8,9-tetrahydro-5H-benzocyclohepten-6-yl)amino]-3-phenoxy-2-propanol (0.59 g) as a crude oil.

IR (Film): 3450, 1759, 1734, 1246 cm$^{-1}$; NMR (CDCl$_3$, δ): 1.22–1.33 (4H, m), 1.45–2.4 (5H, m), 2.5–3.15 (5H, m), 3.45 (1H, m), 3.64–3.95 (4H, m), 4.25 (2H, q, J=7.1 Hz), 4.58 (2H, s), 6.60 (1H, d, J=8.2 Hz), 6.81–7.08 (5H, m), 7.21–7.31 (7H, m); (+) APCI MS m/z: 504 (M$^+$+1).

EXAMPLE 2

The following compound was obtained according to a similar manner to that of Example 1.

(2S)-1-[N-Benzyl-(2-ethoxycarbonylmethoxy-6,7,8,9-tetrahydro-5H-benzocyclohepten-6-yl)amino]-3-phenoxy-2-propanol IR (Film): 3437, 1759, 1738, 1246 cm$^{-1}$; NMR (CDCl$_3$, δ): 1.22–1.45 (4H, m), 1.5–2.25 (4H, m), 2.5–3.05 (7H, m), 3.35 (1H, br), 3.70–3.95 (4H, m), 4.27 (2H, q, J=7.1 Hz), 4.57 and 4.58 (2H, s), 6.58–6.66 (2H, m), 6.83–7.07 (4H, m), 7.21–7.30 (7H, m); (+) APCI MS m/z: 504 (M$^+$+1).

EXAMPLE 3

To a mixture of N-((R)-1-phenylethyl)-((6R)-3-ethoxycarbonylmethoxy-6,7,8,9-tetrahydro-5H-benzocyclohepten-6-yl)amine hydrochloride (2.23 g) in dichloromethane and water was added 1N sodium hydroxide (5.5 ml), and the mixture was stirred for 30 minutes. After separation, the organic layer was dried over anhydrous magnesium sulfate and evaporated in vacuo to give the free amine. Under nitrogen, to a solution of the free amine and (2R)-3-phenoxy-1,2-epoxypropane (0.34 g) in dichloromethane (22 ml) was added ytterbium(III) trifluoromethanesulfonate (0.34 g) at 5°, and the mixture was stirred at room temperature for 1.5 days. The resulting mixture was poured into saturated aqueous sodium bicarbonate solution, and extracted with ethyl acetate. The organic layer was washed with brine, dried over magnesium sulfate, and evaporated in vacuo. The residue was chromatographed (hexane-ethyl acetate) over silica gel to afford (2R)-1-[N-((R)-1-phenylethyl)-((6R)-3-ethoxycarbonylmethoxy-6,7,8,9-tetrahydro-5H-benzocyclohepten-6-yl)amino]-3-phenoxy-2-propanol (2.07 g).

IR (Neat): 3444, 2929, 1758, 1496, 1245, 1166, 1041, 755 cm$^{-1}$; NMR (CHCl$_3$, δ): 1.30 (3H, t, J=7.1 Hz), 1.45 (2H, d, J=6.9 Hz), 1.75–2.10 (3H, m), 2.27 (1H, d, J=12.3 Hz), 2.50–2.85 (4H, m), 3.01 (1H, dd, J=3.5, 13.8 Hz), 3.95–4.05 (4H, m), 4.28 (2H, q, J=7.1 Hz), 4.56 (2H, s), 6.29 (1H, d, J=2.6 Hz), 6.56 (1H, dd, J=2.7, 8.2 Hz), 6.86–7.01 (4H, m), 7.23–7.43 (7H, m).

EXAMPLE 4

To a mixture of N-((S)-1-phenylethyl)-((6S)-3-ethoxycarbonylmethoxy-6,7,8,9-tetrahydro-5H-benzocyclohepten-6-yl)amine hydrochloride (8.1 g) in dichloromethane and water was added 1N sodium hydroxide (20 ml), and the mixture was stirred for 20 minutes. After separation, the organic layer was dried over anhydrous magnesium sulfate and evaporated in vacuo to give the free amine. Under nitrogen, to a solution of the free amine and (2S)-3-phenoxy-1,2-epoxypropane (3.9 g) in dichloromethane (120 ml) was added tin(IV) chloride (1M in dichloromethane, 30 ml) dropwise at −20~−10° C., and the solution was stirred at the same temperature for 1.5 hours. The resulting mixture was poured into 1N hydrogen chloride and extracted with dichloromethane. The organic layer was washed with brine, dried over anhydrous magnesium sulfate and evaporated in vacuo. The residue was chromatographed (hexane-ethyl acetate) over silica gel to give a less polor diastereomer (2S)-1-[N-((S)-1-phenylethyl)-((6S)-3-ethoxycarbonylmethoxy-6,7,8,9-tetrahydro-5H-benzocyclohepten-6-yl)amino]-3-phenoxy-2-propanol (6.65 g) and a more polor diastereomer (2R)-1-[N-((S)-1-phenylethyl)-((6S)-3-ethoxycarbonylmethoxy-6,7,8,9-tetrahydro-5H-benzocyclohepten-6-yl)amino]-3-phenoxy-2-propanol (228 mg).

Less Polar Diastereomer:

IR (Neat): 1758, 1496, 1243, 1195, 1043, 755 cm$^{-1}$; NMR (CHCl$_3$, δ): 1.29 (3H, t, J=7.1 Hz), 1.45 (3H, d, J=6.9 Hz), 1.14–2.03 (4H, m), 2.27 (1H, d, J=12.6 Hz), 2.57–2.82 (5H, m), 3.01 (1H, dd, J=3.6, 13.9 Hz), 3.98–4.14 (4H, m), 4.29 (2H, q, J=7.1 Hz), 4.56 (2H, s), 6.29 (1H, d, J=2.7 Hz), 6.56 (1H, dd, J=2.7, 8.2 Hz), 6.89–6.99 (4H, m), 7.25–7.43 (7H, m); (+) APCI MS (m/z): 518 (M$^+$+1).

More Polar Diastereomer:

IR (Neat): 1758, 1496, 1243, 1195, 1041, 755 cm$^{-1}$; NMR (CHCl$_3$, δ): 1.31 (3H, t, J=7.1 Hz), 1.42 (3H, d, J=6.8 Hz), 1.40–2.19 (4H, m), 2.46–2.99 (7H, m), 3.72–3.83 (1H, m), 3.89–4.15 (4H, m), 4.28 (2H, q, J=7.1 Hz), 4.56 (2H, s), 6.47 (1H, d, J=2.7 Hz), 6.59 (1H, dd, J=2.7, 8.2 Hz), 6.86–7.00 (4H, m), 7.19–7.38 (7H, m); (+) APCI MS (m/z): 518 ($M^+$+1).

EXAMPLE 5

The following compound was obtained according to a similar manner to that of Example 4.

(2S)-1-[N-((R)-1-Phenylethyl)-((6R)-3-ethoxycarbonyl-methoxy-6,7,8,9-tetrahydro-5H-benzocyclohepten-6-yl) amino]-3-phenoxy-2-propanol IR (Neat): 3500, 2929, 1760, 1585, 1500, 1245, 1041, 755 $cm^{-1}$; NMR ($CHCl_3$, δ): 1.31 (3H, t, J=7.1 Hz), 1.42 (2H, d, J=6.8 Hz), 1.45–2.19 (4H, m), 2.46–3.00 (7H, m), 3.74–3.87 (1H, m), 3.93–4.12 (3H, m), 4.28 (2H, d, J=7.1 Hz), 4.56 (2H, s), 6.47 (1H, d, J=2.6 Hz), 6.59 (1H, dd, J=2.7, 8.2 Hz), 6.86–7.00 (4H, m), 7.21–7.38 (7H, m); (+) APCI MS (m/z): 518 ($M^+$+1).

Preparation 3

Under nitrogen, to the solution of 5-methoxy-1-tetralone (25 g) in dichloromethane (125 ml) were added zinc(II) iodide (0.91 g) and trimethylsilyl nitrile (27 ml) at room temperature, and stirred at the same temperature for 12 hours. The resulting mixture was poured into saturated aqueous sodium bicarbonate solution, and extracted with ethyl acetate. The organic layer was washed with saturated aqueous sodium bicarbonate solution, water and brine, dried over anhydrous magnesium sulfate, and evaporated in vacuo to afford 6-methoxy-1-(trimethylsilanyloxy)-1,2,3,4-tetrahydro-naphthalene-1-carbonitrile (41.3 g).

IR (Neat): 2954, 1587, 1467, 1261, 1031, 844 $cm^{-1}$; NMR ($CHCl_3$, δ): 0.02 (9H, s), 1.68–2.18 (4H, m), 2.49 (3H, t, J=6.3 Hz), 3.62 (3H, s), 6.57–7.17 (2H, m).

Preparation 4

Under nitrogen, to the slurry of lithium aluminum hydride (11.4 g) in tetrahydrofuran (200 ml) was added 6-methoxy-1-(trimethylsilanyloxy)-1,2,3,4-tetrahydronaphthalene-1-carbonitrile (41.3 g) in tetrahydrofuran (200 ml) dropwise at 5° C., and the mixture was stirred at the same temperature for 1 hour and at room temperature for 2 hours. To the mixture were added sodium fluoride (12.6 g) and water (16.2 ml) at 5° C., and the mixture was vigorously stirred at room temperature for 30 minutes. The precipitate was removed by filtration and the filter cake was washed with ethyl acetate-ethanol (95:5). The filtrate was evaporated in vacuo to afford 1-aminomethyl-5-methoxy-1,2,3,4-tetrahydronaphthalen-1-ol (28.6 g).

NMR ($CHCl_3$, δ): 1.64–2.12 (4H, m), 2.55–2.82 (2H, m), 2.85 (2H, s), 3.84 (3H, s), 6.76 (1H, dd, J=1.8, 7.3 Hz), 7.05–7.34 (2H, m).

Preparation 5

To a solution of 1-aminomethyl-5-methoxy-1,2,3,4-tetrahydronaphthalen-1-ol (26.6 g) in 1,4-dioxane (60 ml), acetic acid (24 ml) and water (210 ml) was added sodium nitrite (9.7 g) in water (60 ml) dropwise at 5° C., and the mixture was stirred at the same temperature for 2.5 hours. The resulting mixture was diluted with ethyl acetate and separated. The organic layer was washed with saturated aqueous sodium bicarbonate and brine, dried over anhydrous magnesium sulfate, and evaporated in vacuo. The residue was chromatographed (hexane-ethyl acetate) over silica gel to afford 1-methoxy-5,7,8,9-tetrahydro-6H-benzocyclohepten-6-one (12.7 g).

NMR ($CHCl_3$, δ): 1.84–2.04 (2H, m), 2.52 (2H, t, J=7.0 Hz), 2.97–3.04 (2H, m), 3.70 (2H, s), 3.81 (3H, s), 6.76 (1H, d, J=7.7 Hz), 6.81 (1H, d, J=8.4 Hz), 7.13 (1H, t, J=7.9 Hz); (+) APCI MS (m/z): 191 ($M^+$+1), 177.

Preparation 6

A solution of 1-methoxy-5,7,8,9-tetrahydro-6H-benzocyclohepten-6-one (6.0 g) and benzylamine (3.4 ml) in toluene (60 ml) in the presence of a catalytic amount of p-toluenesulfonic acid monohydrate was refluxed for 2 hours to remove water as the toluene azeotrope, and then the mixture was evaporated in vacuo. To the residue in methanol (60 ml) was added sodium borohydride (1.2 g) under nitrogen at 5° C., and the mixture was stirred at room temperature for 12 hours. The resulting mixture was poured into ice-cold water and stirred for 30 minutes before adding ethyl acetate and brine. After separation, the organic layer was washed with brine, dried over anhydrous magnesium sulfate, and evaporated in vacuo. The residue was chromatographed (hexane-ethyl acetate-methanol) over silica gel to afford N-benzyl-(1-methoxy-6,7,8,9-tetrahydro-5H-benzocyclohepten-6-yl)amine (7.27 g).

NMR ($CHCl_3$, δ): 1.32–1.57 (2H, m), 1.70–1.93 (2H, m), 1.95–2.15 (1H, m), 2.58–2.79 (2H, m), 2.88–3.18 (3H, m), 3.78 (3H, s), 3.78 (2H, d, J=13.0 Hz), 3.89 (1H, d, J=13.0 Hz), 6.74 (1H, d, J=8.2 Hz), 6.80 (1H, d, J=7.5 Hz), 7.07 (1H, t, J=7.8 Hz), 7.16–7.37 (5H, (+)APCI MS (m/z): 282 ($M^+$+1).

Preparation 7

Under nitrogen, N-benzyl-(1-methoxy-6,7,8,9-tetrahydro-5H-benzocyclohepten-6-yl)amine (4.5 g) in dichloromethane (45 ml) was added boron tribromide (1M in dichloromethane, 32 ml) dropwise at 0° C., and the mixture was stirred at the same temperature for 2 hours. The resulting mixture was poured into ice-cold water and the precipitate was collected by filtration. The filter cake was added to the mixture of water and ethyl acetate, and then adjusted to pH 9 with 1N sodium hydroxide. After separation, the organic layer was dried over anhydrous magnesium sulfate and evaporated in vacuo to afford N-benzyl-(1-hydroxy-6,7,8,9-tetrahydro-5H-benzocyclohepten-6-yl)amine (3.72 g).

NMR ($CHCl_3$, δ): 1.35–1.57 (1H, m), 1.68–2.13 (3H, m), 2.55–3.08 (5H, m), 3.79 (1H, d, J=12.8 Hz), 3.91 (1H, d, J=12.8 Hz), 6.59 (1H, dd, J=1.2, 7.9 Hz), 6.75 (1H, d, J=6.6 Hz), 6.93 (1H, t, J=7.7 Hz), 7.17–7.36 (5H, m); (+) APCI MS (m/z): 268 ($M^+$+1).

Preparation 8

A solution of 3-methoxy-5,7,8,9-tetrahydro-6H-benzocyclohepten-6-one (10 g) and (R)-1-phenylethylamine (6.8 ml) in toluene (80 ml) in the presence of a catalytic amount of p-toluenesulfonic acid monohydrate (0.10 g) was refluxed for 5 hours to remove water as the toluene azeotrope, and then the mixture was evaporated in vacuo. To the residue in methanol (80 ml) was added Raney nickel (NDT 90, 15 ml) and the mixture was stirred at room temperature in the presence of hydrogen at 3.2–4.0 $kgf/cm^2$ for 15 hours, and filtered. After evaporation in vacuo, the residue was dissolved in ethyl acetate (150 ml). To the solution was added 4N hydrogen chloride in ethyl acetate (26 ml) dropwise at 10–15° C. The mixture was stirred at 5° C. for 1 hour and allowed to stand overnight in a refrigerator. After the mixture was diluted by ether, the precipitate was collected and the filter cake was washed with ether and dried under reduced pressure to afford N-((R)-1-phenylethyl)-(3-methoxy-6,7,8,9-tetrahydro-5H-benzocyclohepten-6-yl) amine hydrochloride (13.7 g).

NMR (DMSO-$d_6$, δ): 0.90–1.19 (1H, m), 1.68 (3H, d, J=6.5 Hz), 1.70–2.10 (2H, m), 2.25–2.75 (4H, m), 2.90–3.33 (2H, m), 3.38–3.70 (3H, s), 4.50–4.95 (1H, m), 6.57–6.85 (2H, m), 6.92–7.05 (1H, m), 7.35–7.53 (3H, m), 7.70–7.88 (2H, m).

Preparation 9

To a mixture of N-((R)-1-phenylethyl)-(3-methoxy-6,7,8,9-tetrahydro-5H-benzocyclohepten-6-yl)amine hydrochloride (13.7 g) in a mixture of ethyl acetate and water was added 28% aqueous ammonium hydroxide (30 ml), and the mixture was stirred for 20 minutes. After separation, the organic layer was washed with brine (twice), dried over anhydrous magnesium sulfate and evaporated in vacuo. To a solution of the residue in 1-propanol (200 ml) was added L-tartaric acid (6.8 g), and the mixture was warmed to 95° C. to dissolve it. Then the solution was slowly cooled to room temperature, and stirred at 5° C. for 1 hour. The precipitate was collected, washed with a little amount of precooled 1-propanol and dried under reduced pressure to afford N-((R)-1-phenylethyl)-((6R)-3-methoxy-6,7,8,9-tetrahydro-5H-benzocyclohepten-6-yl)amine L-tartaric acid (9.47 g).

NMR (DMSO-$d_6$, δ): 0.97–1.25 (1H, m), 1.44 (2H, d, J=6.5 Hz), 1.65–1.95 (2H, m), 1.97–2.15 (1H, m), 2.23–2.37 (1H, m), 2.53–2.75 (1H, m), 2.75–2.95 (1H, m), 3.06 (1H, d, J=13.5 Hz), 3.70 (3H, s), 4.38–4.53 (1H, m), 6.61 (1H, dd, J=2.6, 8.2 Hz), 6.76 (1H, d, J=2.5 Hz), 6.94 (1H, d, J=8.2 Hz), 7.18–7.42 (3H, m), 7.55 (2H, d, J=6.9 Hz).

Preparation 10

A mixture of N-((R)-1-phenylethyl)-((6R)-3-methoxy-6,7,8,9-tetrahydro-5H-benzocyclohepten-6-yl)amine L-tartaric acid (9.47 g) in a mixture of ethyl acetate and water was adjusted to alkali with 28% aqueous ammonium hydoxide and separated. The organic layer was washed with brine, dried over anhydrous magnesium sulfate and evaporated in vacuo. Under nitrogen, to the residue in dichloromethane (140 ml) was added boron tribromide (1M in dichloromethane, 42.5 ml) dropwise at −10∼0° C., and the mixture was stirred at the same temperature for 1 hour. The resulting mixture was poured into ice-cold water with stirring. After stirred at 5° C. for 2 hours, the precipitate was collected. The filter cake was washed with water and dried under reduced pressure to afford N-((R)-1-phenylethyl)-((6R)-3-hydroxy-6,7,8,9-tetrahydro-5H-benzocyclohepten-6-yl)amine hydrobromide (7.78 g).

NMR (DMSO-$d_6$, δ): 0.97–1.23 (1H, m), 1.27–2.01 (3H, m), 1.61 (2H, d, J=6.6 Hz), 2.05–2.65 (3H, m), 2.89 (1H, t, J=10.4 Hz), 3.12 (1H, d, J=13.7 Hz), 4.77–4.96 (1H, br s), 6.49 (1H, dd, J=2.4, 8.1 Hz), 6.66 (1H, d, J=2.4 Hz), 6.86 (1H, d, J=8.1 Hz), 7.37–7.59 (3H, m), 7.65 (2H, d, J=6.5 Hz), 8.74–8.96 (1H, br s), 9.17–9.50 (1H, br s); (+) APCI MS (m/z): 282 (M$^+$+1).

Preparation 11

A mixture of N-((R)-1-phenylethyl)-((6R)-3-hydroxy-6,7,8,9-tetrahydro-5H-benzocyclohepten-6-yl)amine-hydrobromide (7.67 g), ethyl bromoacetate (3.8 ml), potassium carbonate (17.6 g), and tetrabutylammonium chloride (1.18 g) in a mixture of dichloromethane (80 ml) and water (40 ml) was refluxed for 9 hours. After separation, the organic layer was washed with water and brine, dried over anhydrous magnesium sulfate, and evaporated in vacuo. The residue was dissolved in ethyl acetate (90 ml). To the solution was added 4N hydrogen chloride in ethyl acetate (5.6 ml), and the mixture was stirred at 5° C. for 1 hour. The precipitate was collected, washed with a little amount of ice-cold ethyl acetate, and dried under reduce pressure to afford N-((R)-1-phenylethyl)-((6R)-3-ethoxycarbonylmethoxy-6,7,8,9-tetrahydro-5H-benzocyclohepten-6-yl)amine hydrochloride (4.99 g).

NMR (DMSO-$d_6$, δ): 0.95–1.42 (2H, m), 1.23 (3H, t, J=7.1 Hz), 1.46–2.05 (3H, m), 1.67 (3H, d, J=6.5 Hz), 2.26–2.77 (4H, m), 2.99 (1H, t, J=13.4 Hz), 3.13–3.35 (1H, m), 3.37 (2H, s), 4.20 (2H, q, J=7.1 Hz), 4.70 (2H, s), 4.73–4.95 (1H, m), 6.62 (1H, dd, J=2.6, 8.2 Hz), 6.85 (1H, d, J=2.6 Hz), 6.96 (1H, d, J=8.3 Hz), 7.32–7.48 (3H, m), 7.76 (2H, d, J=6.5 Hz), 9.17–9.39 (1H, m), 10.05–10.30 (1H, m); (+) APCI MS (m/z): 368 (M$^+$+1).

EXAMPLE 6

A solution of (2S)-3-phenoxy-1,2-epoxypropane (140 mg) and N-benzyl-(3-ethoxycarbonylmethoxy-6,7,8,9-tetrahydro-5H-benzocyclohepten-6-yl)amine (240 mg) in ethanol (1.36 ml) was stirred under reflux for 2 days, cooled to room temperature, and poured into aqueous sodium bicarbonate solution. The mixture was extracted with ethyl acetate. The extract was washed with water and evaporated in vacuo. The residue was chromatographed (chloroform) over silica gel (10 g) and the eluate was treated with 4N-hydrogenchloride in ethyl acetate to afford (2S)-1-[N-benzyl-(3-ethoxycarbonylmethoxy-6,7,8,9-tetrahydro-5H-benzocyclohepten-6-yl)amino]-3-phenoxy-2-propanol hydrochloride as a crude oil.

A mixture of the crude oil and 10% palladium on activated carbon (50% wet, 150 mg) in ethanol (10 ml) was stirred at room temperature in the presence of hydrogen at an atmospheric pressure and filtered. The filtrate was evaporated in vacuo and the residue was washed with ether to afford (2S)-1-[(3-ethoxycarbonylmethoxy-6,7,8,9-tetrahydro-5H-benzocyclohepten-6-yl)amino]-3-phenoxy-2-propanol hydrochloride (182 mq) as a powder.

mp: 122–128° C.; IR (Nujol): 3340, 3190, 2800–2350, 1740, 1220 cm$^{-1}$; NMR (DMSO-$d_6$, δ): 1.21 (3H, t, J=7.1 Hz, CH$_3$), 1.7–2.8 (8H, m, 4CH$_2$), 2.95–3.3 (3H, m, CH$_2$NCH), 3.9–4.25 (5H, m, OCH$_2$CHO, COOCH$_2$), 4.75 (2H, s, OCH$_2$COO), 5.9 (1H, br s, OH), 6.6–7.35 (8H, m, aromatic H), 8.65–9.2 (3H, m); EI MS (m/z): 413 (M$^+$), 276, 247, 206; Anal. Calcd. for C$_{24}$H$_{31}$NO$_5$.HCl.H$_2$O: C, 61.59, H, 7.32, N, 2.99; Found: C, 61.70, H, 7.03, N, 2.97.

EXAMPLE 7

A solution of 3-(2-allyloxyphenoxy)-1,2-epoxypropane (144 mg) and (S)-7-ethoxycarbonylmethoxy-1,2,3,4-tetrahydro-2-naphthalenamine (obtained from the corresponding hydrochloride (200 mg) in a usual manner) in ethanol (5 ml) was stirred under reflux for 2 hours, cooled to room temperature, and evaporated in vacuo. The residue was chromatographed (ethyl acetate) over silica gel (6.0 g) to afford an oil, which was converted to the oxalate using oxalic acid (35.3 mg) in a usual manner to afford 3-(2-allyloxyphenoxy)-1-[((2S)-7-ethoxycarbonylmethoxy-1,2,3,4-tetrahydronaphthalen-2-yl)amino]-2-propanol oxalate (182 mg) as a powder.

mp: 105–109° C.; IR (KBr): 3325, 3190, 2800–2350, 1736 cm$^{-1}$; NMR (DMSO-$d_6$, δ): 1.21 (3H, t, J=7.1 Hz, CH$_3$), 1.74 (1H, m, CH$_2$), 2.21 (1H, m, CH$_2$), 2.78 (3H, m, CH$_2$), 3.10–3.24 (3H, m, CH$_2$), 3.42 (1H, m, NCH), 3.9–4.05 (3H, m, OCH$_2$CHO), 4.16 (2H, q, J=7.1 Hz, COOCH$_2$), 4.58 (2H, d, J=5.1 Hz, OCH$_2$C=), 4.72 (2H, s, OCH$_2$COO), 5.25 (1H, dd, J=17.4, 1.8 Hz, =CH$_2$), 5.42 (1H, dd, J=17.4, 1.8 Hz, =CH$_2$), 5.6 (1H, br, OH), 5.96–6.14 (1H, m, CH=), 6.65–6.75 (2H, m, aromatic H), 6.88–7.05 (5H, m, aromatic H); EI MS (m/z); 455 (M$^+$), 262.

EXAMPLE 8

A mixture of (2S)-1-[N-benzyl-(1-ethoxycarbonylmethoxy-6,7,8,9-tetrahydro-5H-benzocyclohepten-6-yl)amino]-3-phenoxy-2-propanol (0.55 g) and 10% Pd/C (50% wet, 150 mg) in methanol (6 ml) was stirred at room temperature in the presence of hydrogen at an atmospheric pressure for 4 hours and filtered. The filtrate was evaporated in vacuo and the residue was chromatographed (chloroform-ethanol) over silica gel (8 g) to afford (2S)-1-[(1-ethoxycarbonylmethoxy-6,7,8,9-tetrahydro-5H-benzocyclohepten-6-yl)amino]-3-phenoxy-2-propanol (365 mg) as a pale yellow solid. The solid (109 mg) was treated with 4N hydrogen chloride in ethyl acetate and powdered from ether to afford (2S)-1-[(1-ethoxycarbonylmethoxy-6,7,8,9-tetrahydro-5H-benzocyclohepten-6-yl)amino]-3-phenoxy-2-propanol hydrochloride (96 mg) as a colorless amorphous powder.

mp: 43–58° C.; IR (KBr): 3384, 2800–2350, 1755, 1736, 1246, 1207 cm$^{-1}$; NMR (DMSO-d$_6$, δ): 1.15–1.3 (1H, m), 1.21 (3H, t, J=7.1 Hz), 1.7–2.1 (2H, m), 2.25–2.42 (2H, m), 2.95–3.45 (6H, m), 4.01 (2H, m), 4.15 (2H, q, J=7.1 Hz), 4.22 (1H, m), 4.76 (2H, s), 5.9 (1H, d, J=4.8 Hz), 6.76–7.12 (6H, m), 7.31 (2H, t, J=7.8 Hz), 8.81 (1H, br), 9.12 (1H, br); (+) APCI MS m/z: 414 (M$^+$+1).

EXAMPLE 9

A mixture of (2S)-1-[N-benzyl-(2-ethoxycarbonylmethoxy-6,7,8,9-tetrahydro-5H-benzocyclohepten-6-yl)amino]-3-phenoxy-2-propanol (362 mg) and 10% Pd/C (50% wet, 100 mg) in ethanol (4 ml) was stirred at room temperature in the presence of hydrogen at an atmospheric pressure for 5 hours and filtered. The filtrate was evaporated in vacuo and the residue was chromatographed (dichloromethane-ethanol) over silica gel (6 g) to afford (2S)-1-[(2-ethoxycarbonylmethoxy-6,7,8,9-tetrahydro-5H-benzocyclohepten-6-yl)amino]-3-phenoxy-2-propanol (274 mg) as a pale yellow oil. The oil (95 mg) and oxalic acid (20 mg) were dissolved in ethanol and the solution was evaporated in vacuo. The residue was powdered from ether to afford (2S)-1-[(2-ethoxycarbonylmethoxy-6,7,8, 9-tetrahydro-5H-benzocyclohepten-6-yl)amino]-3-phenoxy-2-propanol oxalate (1;1) (85 mg) as a colorless powder.

mp: 78.5–91.5° C.; IR (KBr): 3442, 3408, 2800–2350, 1753, 1641, 1599, 1241, 1213 cm$^{-1}$; NMR (DMSO-d$_6$, δ): 1.21 (3H, t, J=7.1 Hz), 1.35 (1H, m), 1.8 (1H, m), 2.0 (1H, m), 2.25 (1H, m), 2.69 (2H, m), 2.95–3.25 (5H, m), 3.99 (2H, m), 4.16 (2H and 1H, q (J=7.1 Hz) and m, respectively), 4.72 (2H, s), 5.5 (1H, br), 6.65–6.75 (2H, m), 6.94–6.99 (3H, m), 7.08–7.14 (1H, m), 7.27–7.36 (2H, m) (+) APCI MS (m/z): 414 (M$^+$+1); Anal. Calcd. for C$_{24}$H$_{31}$NO$_5$.C$_2$H$_2$O$_4$.0.2H$_2$O: C, 61.58, H, 6.63, N, 2.76; Found: C, 61.51, H, 6.61, N, 2.71.

EXAMPLE 10

A solution of (2S)-1-[(1-ethoxycarbonylmethoxy-6,7,8,9-tetrahydro-5H-benzocyclohepten-6-yl)amino]-3-phenoxy-2-propanol (103 mg) in methanol (5.0 ml) and 0.1N sodium hydroxide aqueous solution (2.5 ml) was stirred for 22 hours and evaporated in vacuo. The residue was triturated in diethyl ether and the precipitated powder was collected by filtration to afford sodium [6,7,8,9-tetrahydro-6-[((2S)-2-hydroxy-3-phenoxypropyl)amino]-5H-benzocyclohepten-1-yloxy]acetate (98 mg) as a pale yellow powder.

mp: 65° C. (dec.); IR (KBr): 3411, 1599, 1240 cm$^{-1}$; NMR (DMSO-d$_6$, δ): 1.2–2.0 (4H, m), 2.45–2.85 (7H, m), 3.12 (1H, m), 3.75–3.95 (3H, m), 4.05 (2H, s), 5.02 (1H, br d), 6.57 (1H, d, J=8.2 Hz), 6.64 (1H, d, J=7.2 Hz), 6.85–6.94 (4H, m), 7.27 (2H, t, J=8.0 Hz) (+) APCI MS m/z: 386 (M$^+$-Na+2); Anal. Calcd. for C$_{22}$H$_{26}$NO$_5$.H$_2$O: C, 62.11, H, 6.63, N, 3.29; Found: C, 62.31, H, 6.59, N, 3.20.

EXAMPLE 11

The following compound was obtained according to a similar manner to that of Example 10.

Sodium [6,7,8,9-tetrahydro-6-[((2S)-2-hydroxy-3-phenoxypropyl)amino]-5H-benzocyclohepten-2-yloxy] acetate mp: 166–174° C.; IR (KBr): 3431, 1601, 1248 cm$^{-1}$; NMR (DMSO-d$_6$, δ): 1.25–1.95 (4H, m), 2.35–2.85 (7H, m), 3.25 (1H, m), 3.75–4.15 (3H, m), 4.01 (2H, s), 4.99 (1H, br s), 6.48 (1H, dd, J=8.1, 2.5 Hz), 6.55 (1H, d, J=2.5 Hz), 6.87–6.96 (4H, m), 7.27 (2H, t, J=8.0 Hz); (+) APCI MS m/z: 386 (M$^+$-Na+2); Anal. Calcd. for C$_{22}$H$_{26}$N $_5$Na 1.4H$_2$O: C, 61.07, H, 6.71, N, 3.24; Found C, 61.10, H, 6.42, N, 3.14.

EXAMPLE 12

A mixture of (2R)-1-[N-((R)-1-phenylethyl)-((6R)-3-ethoxycarbonylmethoxy-6,7,8,9-tetrahydro-5H-benzocyclohepten-6-yl)amino]-3-phenoxy-2-propanol (2.0 g) and 10% palladium on activated carbon (50% wet, 0.70 g) in ethanol (24 ml) and tetrahydrofuran (12 ml) was stirred at room temperature in the presence of hydrogen at an atmospheric pressure for 3.5 hours, and filtered. The filtrate was evaporated in vacuo. The residue was chromatographed (chloroform-methanol) over silica gel to afford (2R)-1-[((6R)-3-ethoxycarbonylmethoxy-6,7,8,9-tetrahydro-5H-benzocyclohepten-6-yl)amino]-3-phenoxy-2-propanol (1.37 g).

IR (KBr): 1760, 1498, 1249, 1033, 757 cm$^{-1}$; NMR (CHCl$_3$, δ): 1.29 (3H, t, J=7.1 Hz), 1.42–1.67 (1H, m), 1.69–1.90 (2H, m), 1.94–2.13 (1H, m), 2.69–2.97 (7H, m), 3.94–4.05 (3H, m), 4.25 (2H, d, J=7.1 Hz), 4.56 (2H, s), 6.62 (1H, dd, J=2.7, 8.2 Hz), 6.85–7.03 (4H, m), 7.20–7.33 (2H, m); (+) APCI MS (m/z): 414 (M$^+$+1).

EXAMPLE 13

A mixture of (2S)-1-[N-((S)-1-phenylethyl)-((6S)-3-ethoxycarbonylmethoxy-6,7,8,9-tetrahydro-5H-benzocyclohepten-6-yl)amino]-3-phenoxy-2-propanol (0.65 g) and 10% palladium on activated carbon (50% wet, 0.20 g) in ethanol (6 ml) and tetrahydrofuran (3 ml) was stirred at room temperature in the presence of hydrogen at an atmospheric pressure for 1 hour, and filtered. The filtrate was evaporated in vacuo. The residue was chromatographed (chloroform-methanol) over silica gel to afford (2S)-1-[((6S)-3-ethoxycarbonylmethoxy-6,7,8,9-tetrahydro-5H-benzocyclohepten-6-yl)amino]-3-phenoxy-2-propanol (430 mg). (2S)-1-[((6S)-3-Ethoxycarbonylmethoxy-6,7,8,9-tetrahydro-5H-benzocyclohepten-6-yl)amino]-3-phenoxy-2-propanol (190 mg) was treated with 4N hydrogen chloride in ethyl acetate to afford (2S)-1-[((6S)-3-ethoxycarbonyl-methoxy-6,7,8,9-tetrahydro-5H-benzocyclohepten-6-yl) amino]- 3-phenoxy-2-propanol hydrochloride (103 mg).

IR (KBr) 3417, 1754, 1598, 1502, 1245, 1203, 1076, 755 cm$^{-1}$; NMR (DMSO-d$_6$, δ): 1.20 (3H, t, J=7. Hz), 1.17–1.40 (1H, m), 1.72–2.10 (2H, m), 2.19–2.35 (1H, m), 2.66–2.77 (2H, m), 2.98–3.45 (5H, m), 4.01 (2H, d, J=5.1 Hz), 4.16 (2H, q, J=7.1 Hz), 4.11–4.33 (1H, m), 4.71 (2H, s), 5.92 (1H, d, J=4.7 Hz), 6.64–6.73 (1H, m), 6.83 (1H, d, J=2.5 Hz), 6.93–7.08 (4H, m), 7.31 (2H, t, J=7.9 Hz), 8.70–9.15 (2H, m); (+) APCI MS (m/z): 414 (M$^+$+1).

EXAMPLE 14

To a solution of (2S)-1-[((6S)-3-ethoxycarbonylmethoxy-6,7,8,9-tetrahydro-5H-benzocyclohepten-6-yl)amino]-3- phenoxy-2-propanol (249 mg) in ethanol (1 ml) was added 1N sodium hydroxide at 5° C. After stirred at room temperature for 2 hours, the mixture was evaporated in vacuo to afford sodium [(6S)-6-[((2S)-2-hydroxy-3-phenoxypropyl) amino]-6,7,8,9-tetrahydro-5H-benzocyclohepten-3-yloxy] acetate (210 mg).

IR (KBr): 3417, 1610, 1498, 1425, 1247, 1060, 754 cm$^{-1}$; NMR (D$_2$O, δ): 1.35–1.58 (1H, m), 1.65–2.06 (3H, m), 2.59–2.93 (4H, m), 3.89–4.12 (3H, m), 4.41 (2H, s), 6.65 (1H, dd, J=2.6, 8.2 Hz), 6.80 (1H, d, J=2.6 Hz), 6.94–7.09 (5H, m), 7.30–7.42 (2H, m); (+) APCI MS (m/z): 386 (M$^+$–Na+2).

EXAMPLE 15

The following compounds were obtained according to a similar manner to that of Example 13.

(1) (2S)-1-[ ((6R)-3-Ethoxycarbonylmethoxy-6,7,8,9-tetrahydro-5H-benzocyclohepten-6-yl) amino] -3-phenoxy-2-propanol hydrochloride IR (KBr): 3446, 1749, 1504, 1243, 1207, 757 cm$^{-1}$; NMR (DMSO-d$_6$, δ): 1.21 (3H, t, J=7.1 Hz), 1.16–1.38 (1H, m), 1.71–2.12 (2H, m), 2.23–2.37 (1H, m), 2.65–2.74 (2H, m), 2.98–3.16 (4H, m), 3.19–3.30 (1H, m), 4.00 (2H, d, J=5.1 Hz), 4.17 (2H, q, J=7.1 Hz), 4.13–4.32 (1H, m), 4.72 (2H, s), 5.91 (1H, d, J=4.8 Hz), 6.69 (1H, dd, J=2.6, 8.3 Hz), 6.81 (1H, d, J=2.6 Hz), 6.92–7.08 (4H, m), 7.25–7.37 (2H, m), 8.58–8.90 (1H, m), 8.91–9.25 (1H, m); (+) APCI MS (m/z) 414 (M$^+$+1).

(2) (2R)-1-[((6S)-3-Ethoxycarbonylmethoxy-6,7,8,9-tetrahydro-5H-benzocyclohepten-6-yl)amino]-3-phenoxy-2-propanol hydrochloride IR (KBr): 3446, 1749, 1498, 1243 cm$^{-1}$; NMR (DMSO-d$_6$, δ): 1.21 (3H, t, J=7.1 Hz), 1.16–1.43 (1H, m), 1.70–2.13 (2H, m), 2.25–2.39 (1H, m), 2.63–2.75 (2H, m), 2.95–3.38 (5H, m), 4.00 (2H, d, J=5.1 Hz), 4.17 (2H, q, J=7.1 Hz), 4.08–4.32 (1H, m), 4.72 (2H, s), 5.91 (1H, d, J=4.7 Hz), 6.69 (1H, dd, J=2.6, 8.2 Hz), 6.82 (1H, d, J=2.6 Hz), 6.92–7.08 (4H, m), 7.25–7.17 (2H, m), 8.65–8.90 (1H, br s), 8.97–9.28 (1H, br s); (+) APCI MS (m/z): 414 (M$^+$+1).

EXAMPLE 16

The following compounds were obtained according to a similar manner to that of Example 14.

(1) Sodium [(6R)-6-[((2R)-2-hydroxy-3-phenoxypropyl) amino]-6,7,8,9-tetrahydro-5H-benzocyclohepten-3-yloxy] acetate IR (KBr): 3421, 1602, 1498, 1247, 1060, 754 cm$^{-1}$; NMR (D$_2$O, δ): 1.35–1.55 (1H, m), 1.63–2.05 (3H, m), 2.55–2.97 (7H, m), 3.89–4.13 (3H, m), 4.40 (2H, s), 6.64 (1H, dd, J=2.6, 8.2 Hz), 6.79 (1H, d, J=2.6 Hz), 6.90–7.09 (4H, m), 7.25–7.41 (2H, m); MALDI-MS (m/z): 408 (M$^+$+1), 386.

(2) Sodium [(6)-6-[((2R)-2-hydroxy-3-phenoxypropyl) amino]-6,7,8,9-tetrahydro-5H-benzocyclohepten-3-yloxy] acetate IR (KBr): 3444, 1627, 1600, 1500, 1421, 1249, 1058, 752 cm$^{-1}$; NMR (D$_2$O, δ): 0.94–1.17 (1H, m), 1.10–1.70 (3H, m), 2.19–2.65 (7H, m), 3.45–3.72 (3H, m), 3.97 (2H, s), 6.62 (1H, dd, J=2.6, 8.2 Hz), 6.39 (1H, d, J=2.5 Hz), 6.45–6.70 (4H, m), 6.85–6.99 (2H, m); MALDI-MS (m/z): 386 (M$^+$+1).

(3) Sodium [(6R)-6-[((2S)-2-hydroxy-3-phenoxypropyl) amino]-6,7,8,9-tetrahydro-5H-benzocyclohepten-3-yloxy] acetate IR (KBr): 3444, 1600, 1498, 1253, 1245, 1047, 752 cm$^{-1}$; NMR (D$_2$O, δ) 1.37–1.63 (1H, m), 1.66–2.09 (3H, m), 2.63–3.05 (7H, m), 3.94–4.17 (3H, m), 6.66 (1H, dd, J=2.5, 8.2 Hz), 6.82 (1H, d, J=2.5 Hz), 6.93–7.11 (4H, m), 7.31–7.43 (2H, m); (+)APCI MS (m/z): 386 (M$^+$–Na+2).

EXAMPLE 17

The following compound was obtained according to a similar manner to that of Example 12.

(2R)-1-[((6S)-3-Ethoxycarbonylmethoxy-6,7,8,9-tetrahydro-5H-benzocyclohepten-6-yl)amino]-3-phenoxy-2-propanol (137 mg) was obtained.

NMR (CDCl$_3$, δ): 1.29 (3H, t, J=7.1 Hz), 1.45–1.68 (1H, m), 1.71–1.93 (2H, m), 1.95–2.13 (1H, m), 2.30–3.05 (7H, m), 3.94–4.08 (3H, m), 4.26 (2H, q, J=7.1 Hz), 4.58 (2H, s), 6.64 (1H, dd, J=2.7, 8.2 Hz), 6.76 (1H, d, J=2.7 Hz), 6.85–7.03 (4H, m), 7.21–7.33 (2H, m).

The propanolamine derivatives and salts thereof of the object compound [II] including the object compounds of the above-mentioned Examples possess β$_3$ adrenergic receptor stimulating activity and are useful as β$_3$ adrenergic receptor agonists which are effective in the treatment and/or prevention of the aforesaid diseases.

What we claim is:

1. A compound of the formula:

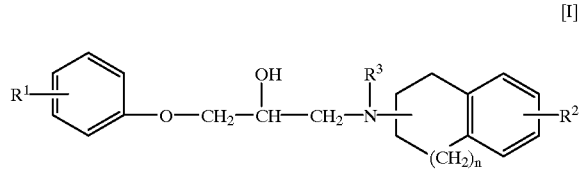

[I]

wherein R$^1$ is hydrogen or lower alkenyloxy,

R$^2$ is carboxy(lower)alkoxy or protected carboxy(lower) alkoxy,

R$^3$ is hydrogen or N-protective group, n is an integer of 1 or 2, and salts thereof.

2. A compound of claim 1, wherein R$^1$ is hydrogen or lower alkenyloxy,

R$^2$ is carboxy(lower)alkoxy or lower alkoxycarbonyl (lower)alkoxy,

R$^3$ is hydrogen or ar(lower)alkyl, and n is an integer of 1 or 2.

3. A process for preparing a compound of the formula:

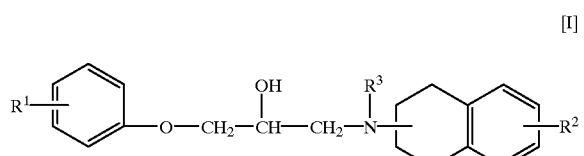

[I]

wherein R$^1$ is hydrogen or lower alkenyloxy,

R$^2$ is carboxy(lower)alkoxy or protected carboxy(lower) alkoxy,

R$^3$ is hydrogen or N-protective group, and n is an integer of 1 or 2, or salts thereof, which comprises (a) reacting a compound of the formula:

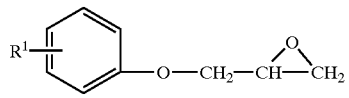

with a compound of the formula:

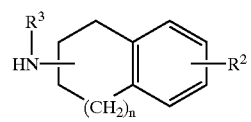

or its salt to provide a compound of the formula:

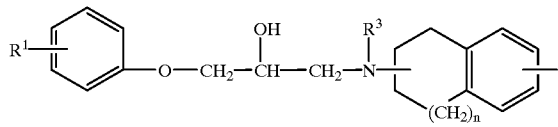

or its salt, in the above formulas, $R^1$, $R^2$, $R^3$ and n are each as defined above, or (b) subjecting a compound of the formula:

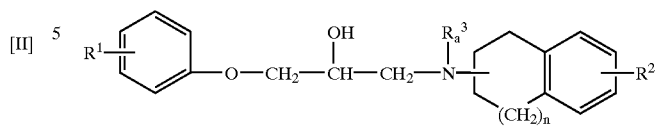

or its salt to elimination reaction of the N-protective group to provide a compound of the formula:

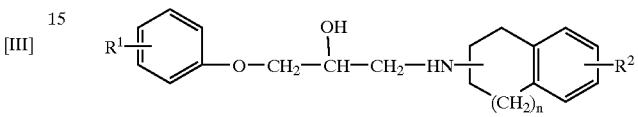

or its salt, in the above formulas,
$R^1$, $R^2$ and n are each as defined above, and
$R_a^3$ is N-protective group.

4. A pharmaceutical composition comprising a compound of claim 1 or pharmaceutically acceptable salt thereof, as an active ingredient, in association with a pharmaceutically acceptable, substantially non-toxic carrier or excipient.

5. A method for the treatment and/or prevention of spasm or hyperanakinesia; gastric ulcer, duodenal ulcer or peptic ulcer caused by non steroidal anti-inflammatory drugs; dysuria; or pancreatitis, obesity, diabetes, glycosuria, hyperlipidemia, hypertension, atherosclerosis, glaucoma, metancholia or depression, which comprises administering the effective amount of a compound of claim 1 or pharmaceutically acceptable salt thereof to human beings or animals.

* * * * *

UNITED STATES PATENT AND TRADEMARK OFFICE
CERTIFICATE OF CORRECTION

PATENT NO.    : 6,391,915 B2
DATED         : May 21, 2002
INVENTOR(S)   : Taniguchi et al.

It is certified that error appears in the above-identified patent and that said Letters Patent is hereby corrected as shown below:

<u>Title page,</u>
Item [30], Foreign Application Priority Data should read:
-- [30]   Foreign Application Priority Data
       Mar. 17, 1997   (AU) ...................................... PO5659 --

Signed and Sealed this

Eighth Day of October, 2002

Attest:

JAMES E. ROGAN
Attesting Officer    Director of the United States Patent and Trademark Office